United States Patent [19]

Kitamura et al.

[11] Patent Number: 4,578,154
[45] Date of Patent: Mar. 25, 1986

[54] METHOD AND APPARATUS FOR MEASURING DISSOLVED GAS CONCENTRATIONS

[75] Inventors: Masao Kitamura, Hitachiota; Norio Nakayama; Ryoei Katsura, both of Hitachi; Hidefumi Ibe, Katsuta; Shunsuke Uchida, Hitachi, all of Japan

[73] Assignees: Hitachi, Ltd.; Hitachi Engineering Co., Ltd., both of Tokyo, Japan

[21] Appl. No.: 746,010

[22] Filed: Jun. 19, 1985

Related U.S. Application Data

[63] Continuation-in-part of Ser. No. 592,801, Mar. 23, 1985, abandoned.

[30] Foreign Application Priority Data

Mar. 25, 1983 [JP] Japan ........................ 58-48646

[51] Int. Cl.$^4$ ............................................. G01N 27/54
[52] U.S. Cl. ............................ 204/1 T; 204/406; 204/408; 204/412; 204/415
[58] Field of Search .......... 204/412, 415, 408, 1 T, 204/1 P, 406

[56] References Cited

U.S. PATENT DOCUMENTS

| 3,325,378 | 6/1967 | Greene et al. | 204/415 X |
| 3,328,277 | 6/1967 | Solomons et al. | 204/412 |
| 3,454,485 | 7/1969 | Hauk et al. | 204/402 |
| 3,503,861 | 3/1970 | Volpe | 204/408 X |
| 3,509,034 | 4/1970 | Paine | 204/415 X |
| 3,649,473 | 3/1972 | Holden | 204/1 T |
| 3,756,923 | 9/1973 | Dahms | 204/1 T |
| 3,767,552 | 10/1973 | Lauer | 204/408 |
| 3,929,603 | 12/1975 | Porter | 204/408 |
| 4,152,233 | 5/1979 | Chand | 204/415 X |
| 4,227,974 | 10/1980 | Petersen et al. | 204/1 T |
| 4,271,474 | 6/1981 | Belanger et al. | 204/415 X |
| 4,293,399 | 10/1981 | Belanger et al. | 204/415 X |
| 4,324,257 | 4/1982 | Albarda et al. | 128/635 |
| 4,333,473 | 6/1982 | Eberhard et al. | 128/635 |
| 4,400,242 | 8/1983 | Albery et al. | 204/415 X |
| 4,435,268 | 3/1984 | Martin et al. | 204/408 |
| 4,452,672 | 6/1984 | Parker et al. | 204/1 T |

FOREIGN PATENT DOCUMENTS 2073430 10/1981 United Kingdom ............ 204/415

OTHER PUBLICATIONS

Michael L. Hitchman, "Measurement of Dissolved Oxygen", pp. 71-121, (1978).

Primary Examiner—G. L. Kaplan
Attorney, Agent, or Firm—Beall Law Offices

[57] ABSTRACT

Two dissolved gas components in sample water, for example, oxygen and hydrogen in core water, are readily quantitatively determined in one and same membrane-type oxygen meter by using a membrane producing an overlapped potential region where a potential region for an oxidation limiting current plateau is overlapped with that for a reduction limiting current plateau between two dissolved gas components, and applying to between a pair of an electrode and a counter-electrode a more positive potential than the equilibrium potential for oxidation-reduction reaction of one of the two dissolved gas components principally, thereby measuring a current generated between the electrodes, and a more negative potential than the equilibrium potential for oxidation-reduction reaction of the other dissolved gas component, when desired, thereby measuring a current generated between the electrodes, and quantitatively determining a concentration of the first dissolved gas component from the latter current quantity and quantitatively determining a concentration of the other dissolved gas component from a difference between the said two current quantities.

20 Claims, 8 Drawing Figures

METHOD AND APPARATUS FOR MEASURING DISSOLVED GAS CONCENTRATIONS

This application is a continuation-in-part of Ser. No. 592,801 filed Mar. 23, 1984 and now abandoned.

BACKGROUND OF THE INVENTION

This invention relates to a method and an apparatus for measuring dissolved gas concentrations, and more particularly to a method and an apparatus for simultaneously measuring a dissolved oxygen concentration and dissolved hydrogen concentration of core water at a high temperature and a high pressure in light water or heavy water-moderated nuclear reactors.

In the present invention, dissolved gas concentrations of core water are measured on a polarographic principle. Measurement of dissolved oxygen concentration is disclosed in U.S. Pat. No. 3,328,277, U.S. Pat. No. 3,454,485, Japanese Patent Application Kokai (laid-open) No. 57-203945, Hitchman, M. L: Measurement of Dissolved Oxygen, published by John Wiley & Sons, Inc. (1978), Chapter 5, etc. Measurement of dissolved oxygen and hydrogen peroxide concentrations is disclosed in Japanese patent application Kokai (laid-open) No. 58-34353, measurement of dissolved $SO_2$ in U.S. Pat. No. 3,756,923, and measurement of dissolved hydrocyanic acid, phosgene, and hydrogen sulfide concentrations in U.S. Pat. No. 4,227,974.

Measurement of dissolved hydrogen concentration in metallic sodium is disclosed in U.S. Pat. Nos. 3,649,473 and 3,683,272 and membranes for measuring dissolved gases in U.S. Pat. No. 3,767,552 and U.K. Patent Application No. GB2073430A.

Measurement of dissolved hydrogen concentration in core water is disclosed by the present applicants in Japanese Patent Application No. 57-97685=U.S. Patent Applicaton Ser. No. 500,367 (now abandoned)-=Canadian Patent Application No. 429637=EPC Patent Application No. 83105626.2.

Figure 1:
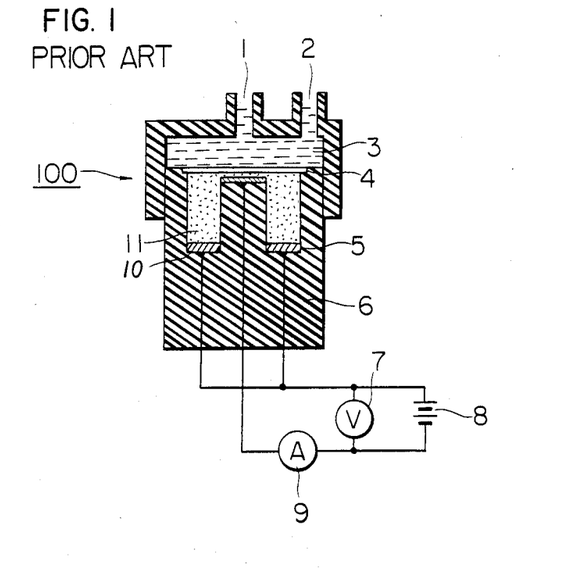
FIG. 1 is a schematic cross-sectional vertical view of a basic structure of a membrane-type, dissolved oxygen meter according to the prior art.

The basic structure of a membrane-type oxygen electrode so far used as a detector for quantitative determination of dissolved oxygen concentration of sample water at room temperature will be described below, referring to FIG. 1, which is a schematic, cross-sectional vertical view of a basic structure of prior art membrane-type dissolved oxygen meter according to the said Hitchman reference.

Oxygen, as dissolved in sample water 3, is continuously supplied to a measuring apparatus 100 from a sample water inlet 1 and discharged therefrom through a sample outlet 2, permeates a membrane 4 into an electrolyte 11, and the oxygen is reduced to $OH^-$ at a working electrode 10 according to the following equation (1) to generate a current between the working electrode 10 and a counter-electrode 5.

$$O_2 + 2H_2O + 4e^- \rightarrow 4OH^- \tag{1}$$

The generated current is measured by an ammeter 9. The working electrode 10 is kept at a desired potential by a potentiometer 7 and a DC current source 8. Basic change in current through a change in the working electrode potential is shown in FIG. 2, which is a characteristic diagram showing changes in output current of the dissolved oxygen meter shown in FIG. 1 through a change in the working electrode potential.

Figure 2:
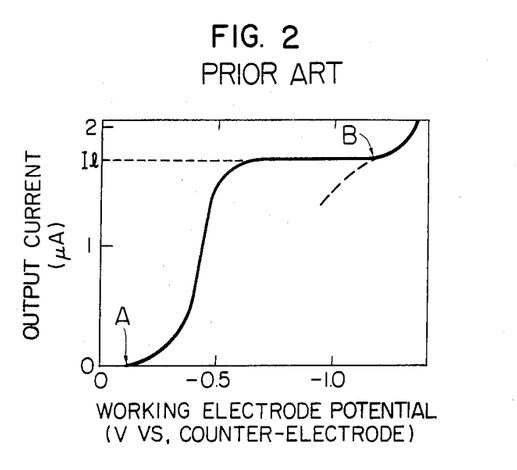
FIG. 2 is a characteristic diagram showing changes in output current of dissolved oxygen meter shown in FIG. 1 with changes in working electrode potential.

In FIG. 2, point A shows an equilibrium potential for oxidation-reduction reaction of oxygen, where no oxygen oxidation or reduction reaction takes place. When the working electrode potential is changed from point A toward more negative direction (toward right side in FIG. 2), the reduction reaction according to equation (1) proceeds to generate reduction current. The electron transfer rate at the electrode surface is a rate-determining factor for the current around the equilibrium potential, and the current is increased with changes in the working electrode potential toward more negative direction, and finally reaches a plateau showing a constant maximum value $I_l$ independent from the potential, where the oxygen permeation rate through the membrane is a rate-determining factor, and the current at the plateau is called "limiting current", which is proportional to an oxygen concentration of sample water. By selecting the potential at any point in this potential region producing the limiting current plateau and measuring a current while keeping the working electrode potential at that potential, dissolved oxygen can be quantitatively determined.

When the potential is made further more negative, the current starts to increase again (point B), because $H^+$ reduction proceeds with the oxygen reduction according to the following equation (2).

$$2H^+ + 2e^- \rightarrow H_2 \tag{2}$$

When there is hydrogen together with oxygen in core water, hydrogen also permeates through the membrane and is oxidized according to the following equation (3) to produce an oxidation current.

$$H_2 \rightarrow 2H^+ + 2e^- \tag{3}$$

It is known that the thus produced hydrogen oxidation current intefere with the oxygen reduction current to reduce the output current by the oxygen reduction, as shown in the dotted line in FIG. 2, resulting in a measurement disturbance. To avoid such disturbance, an oxygen reduction current is measured in the prior art by keeping the working electrode potential around the equilibrium potential of $H_2$ oxidation-reduction reaction as shown by point B in FIG. 2, whereby only a dissolved oxygen concentration is quantitatively determined.

The prior art has thus aimed at eliminating the hydrogen oxidation current as a disturbing current for the measurement of dissolved oxygen, and has not aimed at simultaneous measurement of dissolved hydrogen by utilizing the hydrogen oxidation current at all.

SUMMARY OF THE INVENTION

An object of the present invention is to provide a method and an apparatus for measuring dissolved gas concentrations which are capable of simultaneously measuring dissolved oxygen and hydrogen concentrations of sample water in a temperature range from room temperature to a high temperature, particularly at a high temperature and a high pressure.

The present inventors have found that, when there is dissolved hydrogen together with dissolved oxygen in sample water in the prior art membrane-type dissolved oxygen meter, the hydrogen oxidation current appearing as a disturbing current can also have a potential region producing a limiting current plateau by changing the working electrode potential from the equilibrium potential for hydrogen oxidation-reduction reaction toward more positive direction, and the potential region producing the limiting current plateau of hydrogen oxidation can overlap the potential region producing the limiting current plateau of oxygen reduction by using a membrane permeable to oxygen and hydrogen having an appropriate thickness.

The present invention is based on this finding and provides a method and an apparatus for simultaneously measuring dissolved oxygen and hydrogen concentrations of sample water by using a membrane having a thickness large enough to overlap potential regions producing both limiting current plateaus of hydrogen oxidation and oxygen reduction and measuring a current substantially at the equilibrium potential for hydrogen oxidation-reduction potential, thereby quantitatively determining a dissolved oxygen concentration, and measuring a current at a potential within the overlapped potential region where the potential regions for both limiting current plateaus are overlapped, thereby quantitatively determining a dissolved hydrogen concentration from the difference between the measured current quantities.

According to one aspect of the present invention, an apparatus for measuring dissolved gas concentrations is provided, which comprises a vessel containing an electrolyte, a membrane permeable to a dissolved gas component to be measured provided in the vessel and partitioning the electrolyte from sample water outside the vessel, a pair of an electrode and a counter-electrode being provided in the vessel and dipped in the electrolyte, a power source connected to the electrode and the counter-electrode, and a means for measuring a current generated between the eletrode and the counter-electrode, wherein the membrane is a membrane producing an overlapped potential region where a potential region for an oxidation limiting current plateau is overlapped with that for a reduction limiting current plateau between the two dissolved gas components, and the power source is a power source applying a potential between the electrode and the counter-electrode which potential is a more positive potential than the equilibrium potential for oxidation-reduction reaction of one of the two dissolved gas components principally and a more negative potential than the equilibrium potential for oxidation-reduction reaction of the other dissolved gas component, when desired.

According to another aspect of the present invention, the power source is a power source applying a potential between the electrode and the counter-electrode in the overlapped potential region where the potential region for the oxidation limiting current plateau is overlapped with that for the reduction limiting current plateau between the two dissolved gas components principally and substantially the equilibrium potential for oxidation-reduction reaction of one of the two dissolved gas components, when desired.

According to further aspect of the present invention, a method for measuring dissolved gas components is provided, which comprises providing a membrane permeable to a dissolved gas component to be measured in a vessel containing an electrolyte, thereby partitioning the electrolyte from sample water outside the vessel, dipping a pair of an electrode and a counter-electrode in the electrolyte, and applying a potential to between the electrode and counter-electrode, thereby measuring a current generated between the electrodes, and quantitatively determining a concentration of the gas component therefrom, wherein as the membrane is used a membrane producing an overlapped potential region where a potential range for an oxidation limiting current plateau is overlapped with a potential region for a reduction limiting current plateau between two dissolved gas components, and a more positive potential than the equilibrium potential for oxidation-reduction reaction of one of the two dissolved gas components is applied to between the electrode and the counter-electrode principally, thereby measuring a current generated between the electrodes, and a more negative potential than the equilibrium potential for oxidation-reduction reaction of the other dissolved gas component is applied to therebetween when desired, thereby measuring a current generated between the electrodes, the quantitatively determining a concentration of the first dissolved gas component from the latter current quantity and quantitatively determining a concentration of the other dissolved gas component from a difference between the two current quantities.

According to still further aspects of the present invention, a potential in the overlapped potential region where the potential region for the oxidation limiting current plateau is overlapped with that for the reduction limiting current plateau between the two dissolved gas components is applied principally between the electrode and the counter-electrode, thereby measuring a current generated between the electrodes, and substantially the equilibrium potential for an oxidation-reduction reaction of one of the said two dissolved gas components is applied therebetween, when desired. This measures the current generated between the electrode and quantitatively determines the concentration of the component from the measured current quantity, and quantitatively determines the concentration of the other component from a difference between the said two current quantities.

According to the present invention, the dissolved gas components are preferably oxygen and hydrogen, and the membrane is preferably a polytetrafluoroethylene resin film with a thickness of from 70 $\mu$m to 350 $\mu$m and the applied potential is in the range of about $-0.4$ to $-0.75$. The sample water is core water at a high temperature and a high pressure. The application potential can be adjusted to the desired one by a potential-adjusting means such as a change-over switch or slide wire or the like.

PREFERRED EMBODIMENTS OF THE INVENTION

The present invention will be described in detail below according to embodiments, referring to FIGS. 3 to 8.

Figure 3:
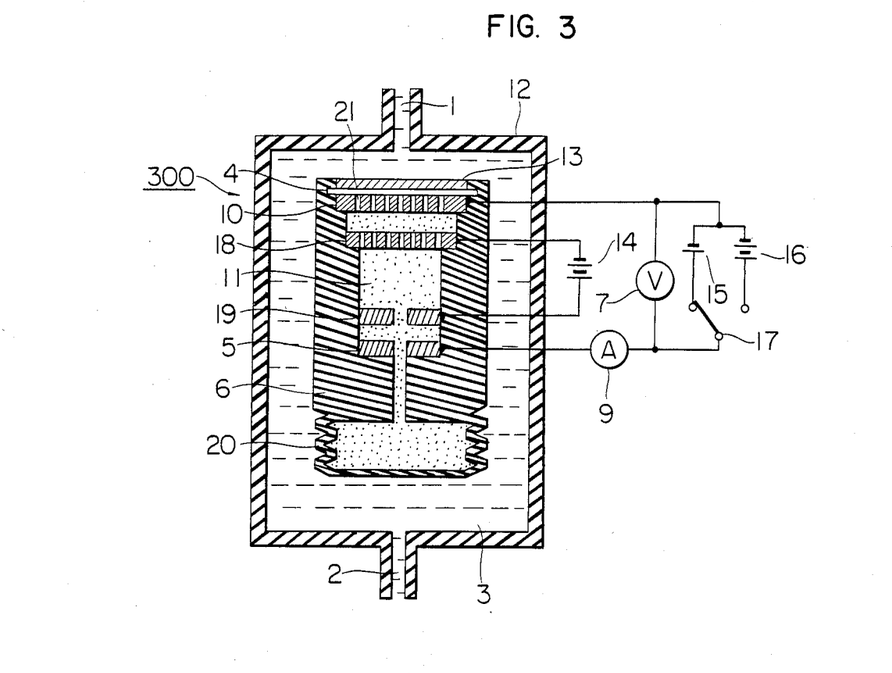
FIG. 3 is a schematic cross-sectional vertical view of one embodiment according to the present invention.

In FIG. 3, one embodiment of a dissolved oxygen-hydrogen meter according to the present invention is schematically shown, and is applicable to determination of dissolved oxygen and hydrogen concentration in sample water not only at room temperature but also at a high temperature and a high pressure. A dissolved oxygen-hydrogen meter 300 comprises a detector body 6, a pressure vessel 12 encasing the detector body 6, and an outside electric circuit including a voltmeter 7, an ammeter 9, a power source 14 for a protective electrode, power sources 15 and 16 for working electrode, and a two-contact switch 17. The outer electric circuit is connected to electrodes (which will be described in detail later) in the detector body 6. The top of the detector body 6 is provided a membrane 4 permeable by oxygen and hydrogen, and the inside of detector body is filled an electrolyte 11. In the electrolyte 11 are provided a porous working electrode 10, a porous protective electrode 18, a counter-electrode 5 for the working electrode and a counter-eletrode 19 for the protective electrode. These electrodes are fixed to the detector body 6. The dissolved oxygen-hydrogen meter is further provided with membranes to improve the durability of the detector because gas concentrations in the sample water at a high temperature must be measured. That is, a bellows 20 is provided at the detector body 6 to absorb the thermal expansion of electroylte 11 in the detector body 6. The membrane 4 is supported at both sides by a porous metallic filter 13 and the porous working electrode 10 to increase the durability of membrane 4. The membrane 4 can be prevented from a damage due to an increasing pressure of electrolyte 11 caused by an increased tension of bellows 20 due to the expansion of bellows 20.

Sample water enters the pressure vessel 12 through a sample water inlet 1 and leaves it through a sample water outlet 2. The pressure vessel 12 is filled with sample water, and a pressure balance is always maintained between the sample water and the electrolyte 11 to prevent the detector body 6 and the membrane 4 from any damage. As described above, the meter can take a measurement even in high temperature and high pressure sample water without damage.

The detector body 6 is made of polytetrafluoroethylene resin, polyimide resin, or other heat-resistant resin. The membrane 4 is a polytetrafluoroethylene resin film having a thickness of 150 μm according to this embodiment. The counter-electrode 5 for working electrode and the counter-electrode 19 for protective electrode are stable, highly reliable Ag/AgCl electrodes with no decomposition even at a high temperature. Consequently, the electrolyte 11 is an alkaline solution containing Cl⁻ ions, for example, an aqueous solution containing 1 mole/l of KOH and 1 mole/l of KCl.

The oxygen and hydrogen in the sample water permeate the membrane 4 into the electroyte 11 in electrode pores 21 of working electrode 10 and are reduced or oxidized on the inside surfaces of electrode pores 21 according to a potential applied to the working electrode 10 during the diffusion in the electrode pores 21, whereby a current is passed between the workin electrode 10 and the counter-electrode 5. A relationship between the current passing between the working electrode 10 and the counter electrode 5 for working electrode and a potential on the working electrode for sample water containing oxygen and hydrogen is shown in FIG. 4.

Figure 4:
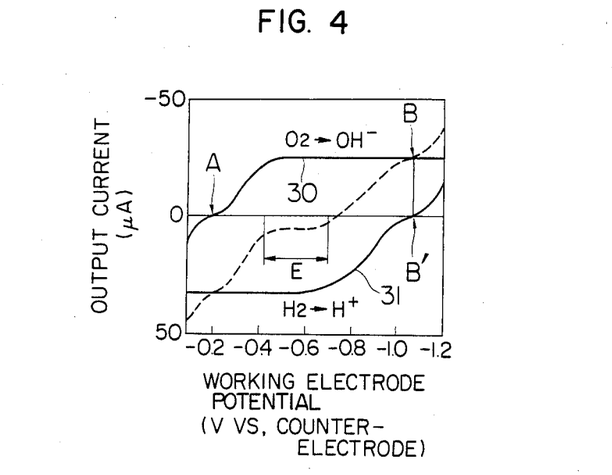
FIG. 4 is a characteristic diagram showing tendencies of output currents obtained when the dissolved oxygen-hydrogen meter shown in FIG. 3 is applied to sample water containing both dissolved oxygen and hydrogen.

In FIG. 4, the reduction current is shown as a negative current. In sample water containing oxygen and hydrogen, a current shown by the dotted line in FIG. 4 is detected, which is produced by interference of the oxygen reduction current with the hydrogen oxidation current. Point A is the equilibriu potential for oxygen oxidation-reduction reaction, as shown in FIG. 2 according to the prior art, and no oxygen oxidation-reduction reaction proceeds at point A. When the potential is made more negative than the equilibrium potential (point A) (toward the right side from point A in FIG. 4), the oxygen reduction reaction proceeds according to the equation (1) to produce a reducing current shown by the full line 30 above in FIG. 4. When the potential is changed toward a still more negative direction, a limiting current plateau of oxygen reduction reaction is obtained. At a more negative potential than point B corresponding to the equilibrium potential for hydrogen oxidation-reduction reaction (at right side from the point B' in FIG. 4), H⁺ reduction reaction starts according to the equation (2) in parallel to the oxygen reduction reaction. The limiting current of oxygen reduction reaction is proportional to a dissolved $O_2$ concentration in sample water. Thus, a dissolved $O_2$ concentration can be quantitatively determined from the limiting current quantity.

As described above, the point B corresponds to the equilibrium potential (point B') for hydrogen oxidation-reduction reaction, and at a more positive potential than the point B the hydrogen oxidation reaction (at the left side from the point B) proceeds according to the equation (3) to produce a hydrogen oxidation current shown by the full line 31 below in FIG. 4. At a further more positive potential, a limiting current plateau of the hydrogen oxidation reaction is produced. The limiting current of the hydrogen oxidation reaction is likewie proportional to a dissolved hydrogen concentration of sample water, and thus a dissolved hydrogen concentration can be quantitatively determined from the limiting current quantity.

Changes in current $I_{O2}$ caused by the oxygen reduction reaction and changes in current $I_{H2}$ caused by the hydrogen oxidation reaction by changes in the working electrode potentials can be given according to the following equations (4) and (5), respectively:

$$I_{O2} = S \cdot \frac{A_{O2} \exp\{d_{O2}(E_O^0 - E)\}}{1 - B_{O2} \exp\{d_{O2}(E_O^0 - E)\}} \quad (4)$$

$$I_{H2} = S \cdot \frac{A_{H2} \exp\{d_{H2}(E_H^0 - E)\}}{1 - B_{H2} \exp\{d_{H2}(E_H^0 - E)\}} \quad (5)$$

where E is a working electrode potential; $E_O^0$ and $E_H^0$ are working electrode potential corresponding to equilibrium potential for oxygen oxidation-reduction reaction and hydrogen oxidation-reduction reaction, respectively; $A_{O2}$, $d_{O2}$ and $B_{O2}$, and $A_{H2}$, $d_{H2}$, and $B_{H2}$ are apparatus constants inherent to the detector and can be determined by measuring an oxygen reduction current is sample water containing only oxygen and a hydrogen oxidation current in sample water containing only hydrogen; S is an area of the membrane and the working electrode. Among them, $A_{O2}$, $d_{O2}$, $A_{H2}$, and $d_{H2}$ are constants depending upon the composition of electrolyte and quality of working electrode, and $B_{O2}$ and $B_{H2}$ have a positive value and are constants which are proportional to the thickness of membrane 4 and inversely proportional to the product of a dissolved oxygen concentration and a membrane permeability coefficient for oxygen and the product of a dissolved hydrogen concentration and a membrane permeability coefficient for hydrogen, respectively. In the equations (4) and (5), the currents $I_{O2}$ and $I_{H2}$ will take constant values independent upon the working electrode potentials in a potential region nearer to the respective equilibrium potentials when the $B_{O2}$ and $B_{H2}$ values are larger, that is, proportionally to the thickness of the membranes. That is, the respective currents have limiting current plateaus.

Between the permeability coefficient P depending upon the material of membrane 4, thickness b of membrane 4 and hydrogen concentration or oxygen concentration c is a relationship represented by the following equation (6); where i is an $O_2$ or $H_2$ membrane permeation rate per unit area:

$$i = Pc/b \quad (6)$$

The limiting current plateau can be obtained at a potential nearer to the equilibrium potential, that is, can be promptly obtained with a lower value of i in the equation (6). In other words, the limiting current plateau can be obtained at a potential nearer to the equilibrium potential with lower permeability coefficient P and concentration c and with larger thickness.

Figure 5:
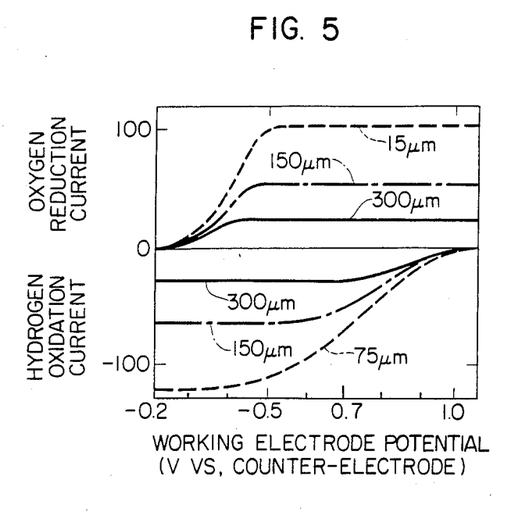
FIG. 5 is a characteristic diagram showing changes in output current with changes in membrane thickness according to the embodiment shown in FIG. 3.

In FIG. 5, changes in potentials producing the limiting current plateau with changes in thickness of membrane 4 are shown, where the membrane 4 is made of polytetrafluoroethylene resin and sample water has a temperature of 285° C. and a dissolved oxygen concentration of 1.2 ppm and a dissolved hydrogen concentration of 0.12 ppm. Both oxygen reduction reaction and hydrogen oxidation reaction have limiting current plateaus at a potential nearer to the equilibrium potential with larger thickness of the membrane. It is seen from FIG. 5 that a suitable overlapped potential for membranes having a thickness of 75 μm, 150 μm, or 300 μm is in the range of −0.5 to −0.6 V, −0.4 to −0.65 V, or −0.4 to 0.75 V, respectively.

Figure 6:
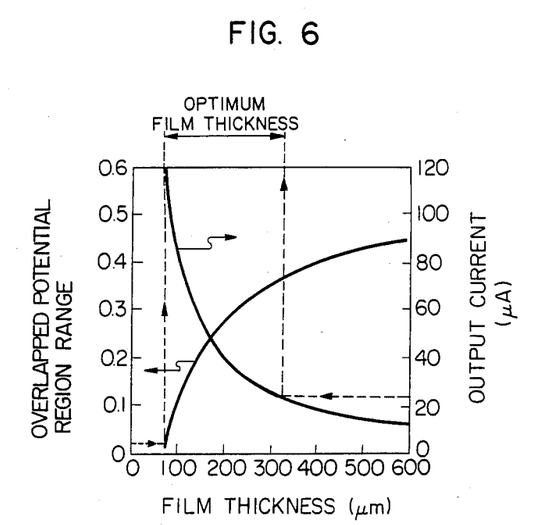
FIG. 6 is a characteristic diagram showing a relationship between the membrane thickness, potential producing overlapped limiting current plateaus, and output current according to the embodiment shown in FIG. 3.

In FIG. 6, a relationship between the potential region producing an overlapped limiting current plateau range, the output current and the thickness of membrane is shown, where the same sample water as used in relation to FIG. 5 is used. When a lower limit dissolved oxygen concentration of sample water is 5 ppb, the lower limit output current must be at least 0.1 μA. At the dissolved oxygen concentration of 1.2 ppm, the output current must be at least 24 μA. From FIG. 6, it is seen that the desirable thickness of membrane is not more than 350 μm. A minimum potential for the overlapped potential region for the limiting current plateau is desirably 0.02 V in view of operating easiness. It is obvious from FIG. 6 that the thickness of membrane is desirably at least about 70 μm. Thus, the desirable thickness of polytetrafluoroethylene resin film for producing the overlapped potential region is 70 μm to 350 μm for sample water at 285° C. Thus, a suitable overlap potential for membrane thickness in the range of 70 to 350 μm, is in the range of −0.4 to −0.75 V.

For measurement of a dissolved oxygen concentration and a dissolved hydrogen concentration of sample water, the potentials of power source 15 and power source 16 for the working electrode in FIG. 3 are adjusted to any value in the overlapped potential region E for the limiting current plateaus and to point B in FIG. 4. Any potential in the overlapped potential region E for the limiting current plateaus can produce both limiting currents for hydrogen oxidation reaction and oxygen reduction reaction. The point B is a point corresponding to point B', the equilibrium potential for the hydrogen oxidation-reduction reaction, as described above. Initially, the turnover switch 17 is connected to the power source 15 for the working electrode to apply the potential in the overlapped potential region E for the limiting current plateaus to the working electrode 10 and measure an output current $I_E$. The measured current $I_E$ is the sum total of limiting current for the oxidation reduction reaction and that for the hydrogen oxidation reaction. Then, the turnover switch 17 is connected to the power source 16 for working electrode to apply the potential at point B to the working electrode 10 to measure a current $I_B$. At the point B, no hydrogen oxidation proceeds, and the current $I_B$ contains no hydrogen oxidation current and is the limiting current for oxygen reduction reaction. A dissolved oxygen concentration can be quantitatively determined from the current $I_B$.

As is obvious from FIG. 4, a dissolved hydrogen concentration can be quantitatively determined from a difference $I_D$ between the current quantities $I_E$ and $I_B$ according to the following equation (7).

$$I_D = I_E - I_B \quad (7)$$

Figure 7:
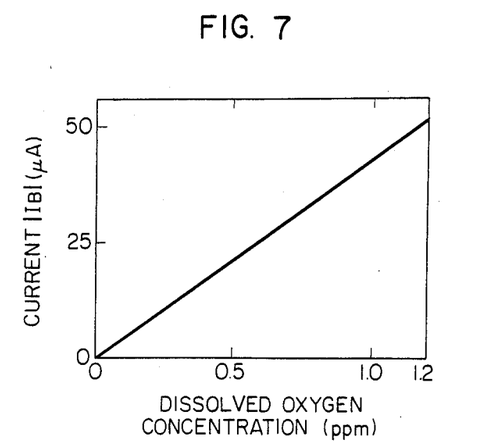
FIG. 7 is a characteristic diagram showing a relationship between the output current $|I_B|$ and the dissolved oxygen concentration according to the embodiment shown in FIG. 3.
Figure 8:
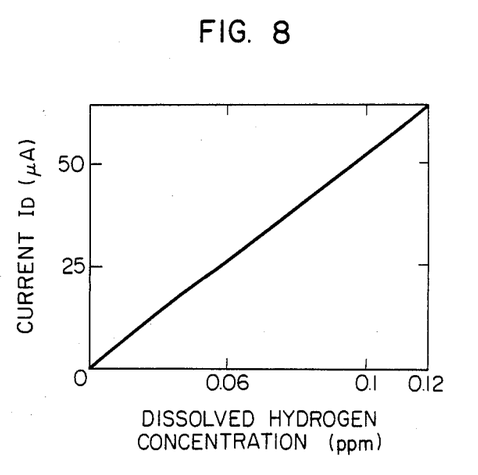
FIG. 8 is a characteristic diagram showing a relationship between the output current $I_D$ and the dissolved hydrogen concentration according to the embodiment shown in FIG. 3.

Relationships between $I_B$ and a dissolved oxygen concentration and between $I_D$ and a dissolved hydrogen concentration as measured in sample water at 285° C. using a polytetrafluoroethylene resin membrane having a thickness of 150 μm are shown in FIG. 7 and FIG. 8, respectively.

The electrolyte 11 in the detector body 6 contains oxygen dissolved from air or impurity ions involved when the electrolyte is sealed therein. Furthermore, $Ag^+$ ions, etc. are dissolved out of AgCl formed by electrode reaction on the surface of counter-electrode 5 for working electrode as the operating temperature is increased, and are accumulated in the electrolyte. These impurity ions diffuse onto the surface of the working electrode 10 and are reduced by the working electrode 10 to generate a disturbing current. To prevent such a disturbing current, a protective electrode 18 and a counter-electrode 19 for the protective electrode are provided in the electrolyte 11 and the disturbing components are moved by reduction at the protective electrode 18.

If the working electrode is kept at the potential at point B for a long time, the hydrogen permeated into the electrolyte 11 from the sample water is not oxidized by the working electrode 10 and accumulates in the electrolyte 11 to give an error to the quantitative determination of a dissolved hydrogen concentration. Thus, immediately after measurement at point B, the applied potential must be lowered to a potential in the overlapped potential region E for the limiting current plateaus and kept at that potential in principle. That is, a potential at point B is applied only when a dissolved oxygen concentration is measured.

In this embodiment, a polytetrafluoroethylene resin membrane having a thickness of 150 $\mu$m is exemplified, but a polytetrafluoroethylene resin membrane having a thickness of 70 $\mu$m to 350 $\mu$m can be used, as shown in FIG. 6. Membranes of other heat-resistant resins having high oxygen and hydrogen permeability coefficients such as polyimide, silicone rubber, etc can be used.

When a membrane having a larger thickness is used, the oxygen and hydrogen-permeating rates are decreased, and consequently output current is reduced. However, an output current is proportional to the area of membrane and working electrode, and thus an improvement can be made by increasing the area of membrane and working electrode.

In this embodiment, the dissolved oxygen concentration and dissolved hydrogen concentration of sample water are exemplified by 1.2 ppm and 0.12 ppm, respectively, but higher dissolved oxygen and hydrogen concentrations can be quantitatively determined by increasing the thickness of membrane, that is, by decreasing the diffusion rate. In a light water-moderated nuclear reactor, the dissolved oxygen concentration and a dissolved hydrogen concentration are 1.0 ppm or less and 0.1 ppm or less. The polytetrafluoroethylene membrane having the thickness of 150 $\mu$m can be well applied to the measurement of core water from the light water-moderated nuclear reactor.

As the counter-electrode, $Ag/AgBr$, $Ag/Ag_2SO_4$, $Ag/Ag_3PO_3$, $Pb/PbSO_4$, etc. have a high reliability at a high temperature and can be used besides the Ag/AgCl electrode, where aqueous solutions correspondingly containing $Br^-$ ions, $SO_4^{2-}$ ions, $PO_3^{3-}$ ions, etc. are to be used as the electrolyte. As the working electrode gold is used. Other oxidation-resistant, noble metals, such as platinum, indium, etc. can be used.

In the present invention, it is also possible to measure a current not only at the equilibrium potential for hydrogen oxidation-reduction potential, but also at a more negative potential than the equilibrium potential, thereby determining a dissolved oxygen concentration therefrom, and determine a dissolved hydrogen concentration from a difference between the current quantity measured at a potential in the overlapped potential region E for the limiting current plateaus and the front current quantity. In the latter case, the current quantity due to the $H^+$ reduction reaction must be subtracted from the first current quantity, for the quantitative determination.

Even from a current measured at a more positive potential than the equilibrium potential for hydrogen oxidation-reduction reaction, so long as the resulting hydrogen oxidation current is within a range of allowable errors for the limiting current for the oxygen reduction reaction, and from a current measured at a potential in the overlapped potential region E for the limiting current plateaus, it is possible to quantitatively determine the dissolved oxygen concentration and hydrogen concentration.

In the foregoing embodiment, an oxygen limiting current is measured at point B to determine a dissolved oxygen concentration and a dissolved hydrogen concentration is determined from a difference between the current quantity measured at a potential in the overlapped potential region E for the limiting current plateaus and the first current quantity, but it is also possible to determine a dissolved hydrogen concentration from the limiting current for the hydrogen oxidation reaction at point A and then determine a dissolved oxygen concentration from a difference between the current quantity measured at a potential in the overlapped potential region E for the limiting current plateaus and the first current quantity. In this case, it is also possible to measure a current at a more positive potential than the equilibrium potential for the oxygen oxidation-reduction reaction to determine a dissolved hydrogen concentration therefrom, or it is also possible to measure a current even at a more negative potential than the equilibrium potential for the oxygen oxidation-reduction reaction, so long as the resulting oxygen reduction current is within a range of allowable errors for the limiting current for the hydrogen oxidation reaction to determine a dissolved hydrogen concentration and also to determine a dissolved oxygen concentration from a difference between the current quantity measured at a potential in the overlapped potential region E for the limiting current plateaus and the first current quantity.

In the foregoing embodiment, a turnover switch means is used to give different potentials to the working electrode, and other potential-adjusting means such a slide wire, etc. can be used for applying different potentials.

In the present invention, dissolved oxygen and hydrogen concentrations of sample water at a high temperature and a high pressure can be effectively measured in one and same detector without cooling the sample water, and thus an apparatus for measuring dissolved oxygen and hydrogen concentrations can be considerably simplified. The present invention is also applicable to a detector for measuring dissolved oxygen and hydrogen in sample water at the core water temperature. Core water in a light water-moderated nuclear reactor contains oxygen, hydrogen, hydrogen peroxide, etc. and the oxygen and hydrogen concentrations are changed during the cooling operation of sample water sampled from the core water through recombination of hydrogen peroxide with hydrogen, thermal decomposition of hydrogen peroxide to oxygen and water, etc. In the present invention, the dissolved oxygen and hydrogen concentrations can be measured directly without cooling sample water.

In the present invention, dissolved oxygen and hydrogen concentrations of sample water at a high temperature and a high pressure sample from core water can be directly measured in a single detector, and thus the present invention can provide a very useful means for controlling a hydrogen dosage to core water or controlling core water quality. In the present invention, dissolved oxygen and hydrogen concentrations of sample water can be readily determined by a single detector.

What is claimed is:
1. An apparatus for measuring dissolved oxygen and hydrogen gas concentrations which comprises:
an electrode;
a counter-electrode;
a vessel filled with electrolyte into which the electrodes are immersed;
an oxygen and hydrogen permeable membrane having a thickness in the range of 70 $\mu$m to 350 $\mu$m partitioning said electrolyte from sample water containing said dissolved gases outside of said vessel;

at least one power source applying a potential in the range of −0.4 to −0.75 V and connecting said electrode and said counter electrode;

means measuring current generated between said electrode and said counter electrode; and wherein the thickness of the membrane determines a potential region for a reduction limiting current plateau and a potential region for an oxidation limiting current plateau between two dissolved gas components to be measured, the combination of both of said regions producing an overlapped potential region.

2. An apparatus according to claim 1, wherein another pair of an electrode and a counter-electrode are further provided between the pair of said electrode and the counter-electrode in the vessel as protective electrodes and dipped in the electrolyte and another power source is provided and connected to said another electrode and counter-electrode.

3. An apparatus according to claim 1 or 2, wherein the two dissolved gas components are oxygen and hydrogen.

4. An apparatus according to claim 1, wherein the membrane is a polytetrafluoroethylene resin film.

5. An apparatus according to claim 1, wherein the sample water is nuclear reactor core water at a temperature of about 285° C.

6. An apparatus according to claim 1, wherein the power source is provided with a change-over switch or a slide wire for adjusting an applying potential.

7. An apparatus according to claim 1, wherein the power source applies a potential in the range of −0.4 to −0.75 V which produces said overlapped potential region to be measured by said current measuring means and then applies a potential which is the oxidation reduction equilibrium potential for one of said two gas components which produces a second current to be measured by said current measuring means.

8. An apparatus according to claim 1 wherein the membrane is supported on one side by a porous metallic filter and on the other side by said electrode which is also porous.

9. An apparatus according to claim 1 wherein the vessel is provided with an expandable bellows to absorb any thermal expansion of the electrolyte.

10. An apparatus according to claim 1 wherein the electrode material is selected from the group consisting of gold, platinum and indium and the counter-electrode material is selected from the group consisting of Ag/AgBr, Ag/AgCl, Ag/Ag$_2$SO$_4$, Ag/Ag$_3$PO$_3$, and Pb/PbSO$_4$ and further wherein the electrolyte is an aqueous solution containing at least one of Br ions, SO$_4^{2-}$ ions and PO$_3^{3-}$ ions.

11. An apparatus according to claim 1 wherein the electrolyte comprises KCl.

12. An apparatus according to claim 1 wherein the permeability coefficient of said membrane is a factor affecting the potential regions for said reduction limiting current plateau and said oxidation current limiting plateau.

13. A method for measuring dissolved oxygen and hydrogen gas components comprising:

providing a sample water containing two dissolved gas components to be measured;

providing a membrane having a thickness in the range of 70 μm to 350 μm permeable by said dissolved gas components, the thickness of said membrane determining and a potential region for a reduction limiting current plateau and a potential region for an oxidation limiting current plateau between said two dissolved gases, the combination of both of said regions producing an overlapped potential region, said membrane separating a vessel from said sample water, said vessel being filled with electrolyte and containing an electrode and a counter-electrode immersed in said electrolyte and connected by a power source;

applying a first potential in the range of −0.4 to −0.75 V from said power source to produce said overlapped potential region and measuring a first current between the electrodes;

applying a second potential from said power source which is the oxidation-reduction equilibrium potential for one of the gases to be measured and measuring a second current between the electrodes to determine the concentration of said one of said gases; and determining the concentration of the remaining one of said two dissolved gases by the difference between said first and second currents.

14. A method according to claim 13, wherein the dissolved gas components are oxygen and hydrogen.

15. A method according to claim 13, wherein the membrane is a polytetrafluoroethylene resin membrane.

16. A method according to claim 13, wherein the sample water is nuclear reactor core water at a temperature of about 285° C.

17. A process according to claim 13 wherein the electrode material is selected from the group consisting of gold, platinum and indium and the counter-electrode material is selected from the group consisting of Ag/AgBr, Ag/AgCl, Ag/Ag$_2$SO$_4$, Ag/Ag$_3$PO$_3$, and Pb/PbSO$_4$ and further wherein the electrolyte is an aqueous solution containing at least one of Br ions, SO$_4^{2-}$ ions and PO$_3^{3-}$ ions.

18. A process according to claim 13 wherein the electrolyte comprises KCl.

19. A process according to claim 13 wherein the permeability coefficient of said membrane is a factor affecting the potential regions for said reduction limiting curent plateau and said oxidation current limiting plateau.

20. A method for measuring dissolved oxygen and hydrogen gas components in a sample water comprising:

providing a sample water containing dissolved hydrogen and oxygen gases;

providing a membrane having a thickness in the range of 70 to 350 μm and permeable by said dissolved hydrogen and oxygen, the thickness of said membrane determining a potential region for an oxygen reduction limiting current plateau and a potential region for a hydrogen oxidation limiting current plateau, the combination of both of said regions producing an overlapped potential region, said membrane separating a vessel filled with electrolyte from said sample water and containing an electrode and a counter electrode immersed in said electrolyte and connected by a power source;

applying a first potential in the range of −0.4 to −0.75 V from said power source to produce said overlapped potential region and measuring a first current between the electrodes;

applying a second potential from said power source which is the oxidation-reduction equilibrium potential for a dissolved oxygen gas, and measuring a second current between the electrodes to determine the concentration of said oxygen gas; and determining the concentration of the dissolved hydrogen by the difference between said first and said second currents.

* * * * *